United States Patent [19]

Duffett et al.

[11] Patent Number: Plant 6,399

[45] Date of Patent: Nov. 15, 1988

[54] CHRYSANTHEMUM PLANT NAMED VERO

[75] Inventors: William E. Duffett; Cornelis P. VandenBerg, both of Salinas, Calif.

[73] Assignee: Yoder Brothers, Inc., Barberton, Ohio

[21] Appl. No.: 5,762

[22] Filed: Jan. 21, 1987

[51] Int. Cl.[4] ..... A01H 5/00
[52] U.S. Cl. ..... Plt./74
[58] Field of Search ..... Plt./74

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Vero particularly characterized by its flat capitulum form; daisy capitulum type; white ray floret color; diameter across face of capitulum of up to 8 cm at maturity; uniform nine week photoperiodic flowering response to short days; medium plant height when grown single stem; 15 to 20 cm peduncles on open, terminal sprays; and by its 13 degrees Celsius minimum temperature tolerance for initiation and development of flowering buds with a 12 to 13 hour continuous dark period.

3 Drawing Sheets

The present invention comprises a new and distinct cultivar of Chrysanthemum, botanically known as *Chrysanthemum morifolium*, Ramat., and referred to by the cultivar name Vero.

Vero, identified as 81064002, was originated from a cross made in a controlled breeding program in Salinas, Calif. in 1981.

The female parent and the male parent of Vero were both unnamed seedlings.

Vero was discovered and selected as one flowering plant within the progeny of the stated cross by William E. Duffett in August 1981 in a controlled environment in Salinas, Calif.

The first act of asexual reproduction of Vero was accomplished when vegetative cuttings were taken from the initial selection in December 1981 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Vero are firmly fixed and are retained through successive generations of asexual reproduction.

Vero has not been observed under all possible environmental conditions. The phenotype may vary significantly with variations in environment such as temperature, light intensity and daylength.

The following observations, measurements and comparisons describe plants grown in Salinas, Calif. and Bogota, Colombia under greenhouse conditions which approximate those generally used in commercial greenhouse practice.

The following traits have been repeatedly observed and are determined to be basic characteristics of Vero, which, in combination, distinguish this Chrysanthemum as a new and distinct cultivar:

1. Flat capitulum form.
2. Daisy capitulum type.
3. White ray floret color.
4. Diameter across face of capitulum of up to 8 cm at maturity.
5. Uniform nine week photoperiodic flowering response to short days.

6. Peduncle length ranging from 15 to 20 cm on open terminal sprays.
7. Medium plant height, requiring two long day weeks prior to short days to attain a flowered plant height of 100 to 110 cm for year-round flowerings.
8. Low temperature tolerance of 13 degrees Celsius for initiation and development when grown in single stem cut spray programs with a continuous dark period of 12 to 13 hours.

The accompanying photographic drawings show typical inflorescence and leaf characteristics of Vero, with the colors being as nearly true as possible with illustrations of this type.

Sheet 1 is a color photograph of Vero grown as a single stem cut spray mum.

Sheet 2 is a black and white photograph of three views of the inflorescence of Vero.

Sheet 3 is a black and white photograph showing the upper and under sides of the leaves of Vero at three stages of development (mature, intermediate and immature).

Of the commercial cultivars known to the inventors, the most similar in comparison to Vero is White Marble. Reference is made to attached Chart A, which compares certain characteristics of Vero to the same characteristics of White Marble.

Similar traits are capitulum form and type, ray floret color, plant height and low temperature tolerance. The peduncle length of Vero is shorter than that of White Marble. Vero has a slightly smaller diameter of capitulum than White Marble. Under adverse conditions White Marble exhibits compounding of the spray formation and develops bract tissue in the disc. The spray formation of Vero is always terminal, with no development of bracts. Vero has a better flower form retention than White Marble. Flowering response to short days of Vero is 3 to 5 days faster than that of White Marble, with a superior uniformity of flowering than White Marble.

In the following description, color references are made to The Royal Horticultural Society Colour Chart. The pure white ray floret color of Vero is not represented in The Royal Horticultural Society Colour Chart. The color values were determined on plant material grown in Salinas, Calif. on Aug. 21, 1986.

Classification:

*Botanical.*—*Chrysanthemum morifolium,* Ramat., cv. Vero.

*Commercial.*—Daisy cut spray mum.

INFLORESCENCE

A. Capitulum:

*Form.*—Flat.

*Type.*—Daisy.

*Diameter across face.*—Up to 8 cm at maturity.

B. Corolla of ray florets:

*Color (general tonality from a distance of three meters).*—White.

*Color (upper surface).*—White.

*Color (under surface).*—White.

*Shape.*—Flat, oblong.

C. Corolla of disc florets:

*Color (mature).*—14A to 14B.

*Color (immature).*—145A.

D. Reproductive organs:

*Androecium.*—Present on disc florets only; scant pollen.

*Gynoecium.*—Present on both ray and disc florets.

PLANT

A. General appearance:

*Height.*—Medium; 100 to 110 cm as a flowering plant from a rooted cutting with fourteen long days for year-round flowerings maintaining a continuous dark period of 12 to 13 hours.

B. Foliage:

*Color (upper surface).*—147A.

*Color (under surface).*—147B.

*Shape.*—Lobed, slightly serrated.

CHART A

COMPARISON OF VERO AND WHITE MARBLE

| CULTIVAR | RAY FLORET COLOR | CAPITULUM FORM & TYPE | SPRAY FORMATION |
|---|---|---|---|
| VERO | WHITE | FLAT DAISY | TERMINAL 15 to 20 cm PEDUNCLES |
| WHITE MARBLE | WHITE | FLAT DAISY | TERMINAL to COMPOUND 20 to 25 cm PEDUNCLES |

| CULTIVAR | DIAMETER ACROSS FACE OF CAPITULUM | PLANT HEIGHT | FLOWERING RESPONSE PERIOD |
|---|---|---|---|
| VERO | up to 8 cm | MEDIUM | 9 WEEKS |
| WHITE MARBLE | up to 9 cm | MEDIUM | 9 to 10 WEEKS |

| CULTIVAR | TOLERANCE OF 13 C |
|---|---|
| VERO | GOOD |
| WHITE MARBLE | GOOD |

COMPARISONS MADE OF PLANTS GROWN AS SINGLE STEM SPRAY CUT MUMS WITH 14 LONG DAYS IN SALINAS, CALIFORNIA AND IN BOGOTA, COLUMBIA

We claim:

1. A new and distinct plant of Chrysanthemum named Vero, as described and illustrated, and particularly characterized as to uniqueness by the combined characteristics of flat capitulum form; daisy capitulum type; white ray floret color; diameter across face of capitulum of up to 8 cm at maturity; uniform nine week photoperiodic flowering response to short days; medium plant height when grown single stem; 15 to 20 cm peduncles on open, terminal sprays; and 13 degrees Celsius minimum temperature tolerance for initiation and development of flowering buds.

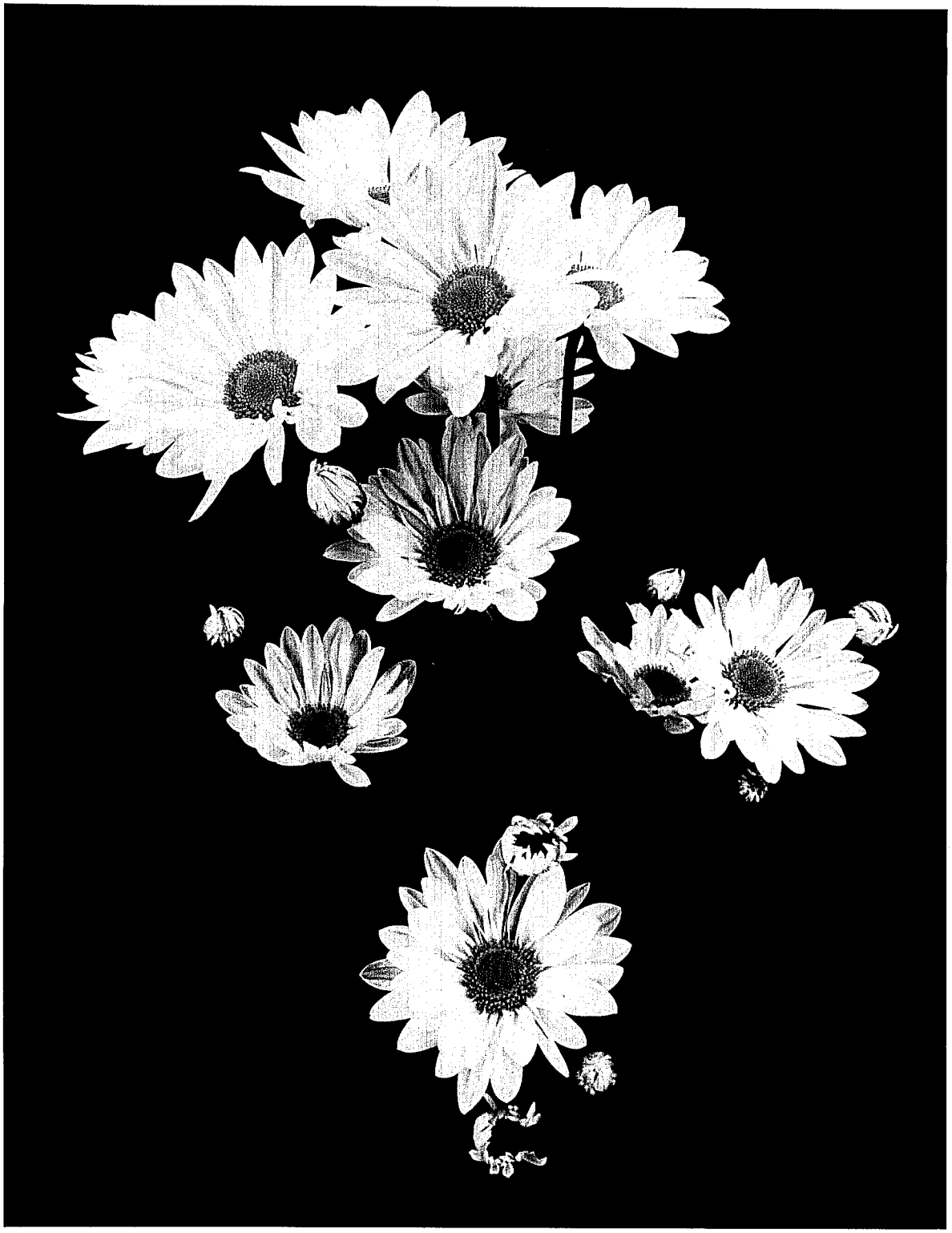

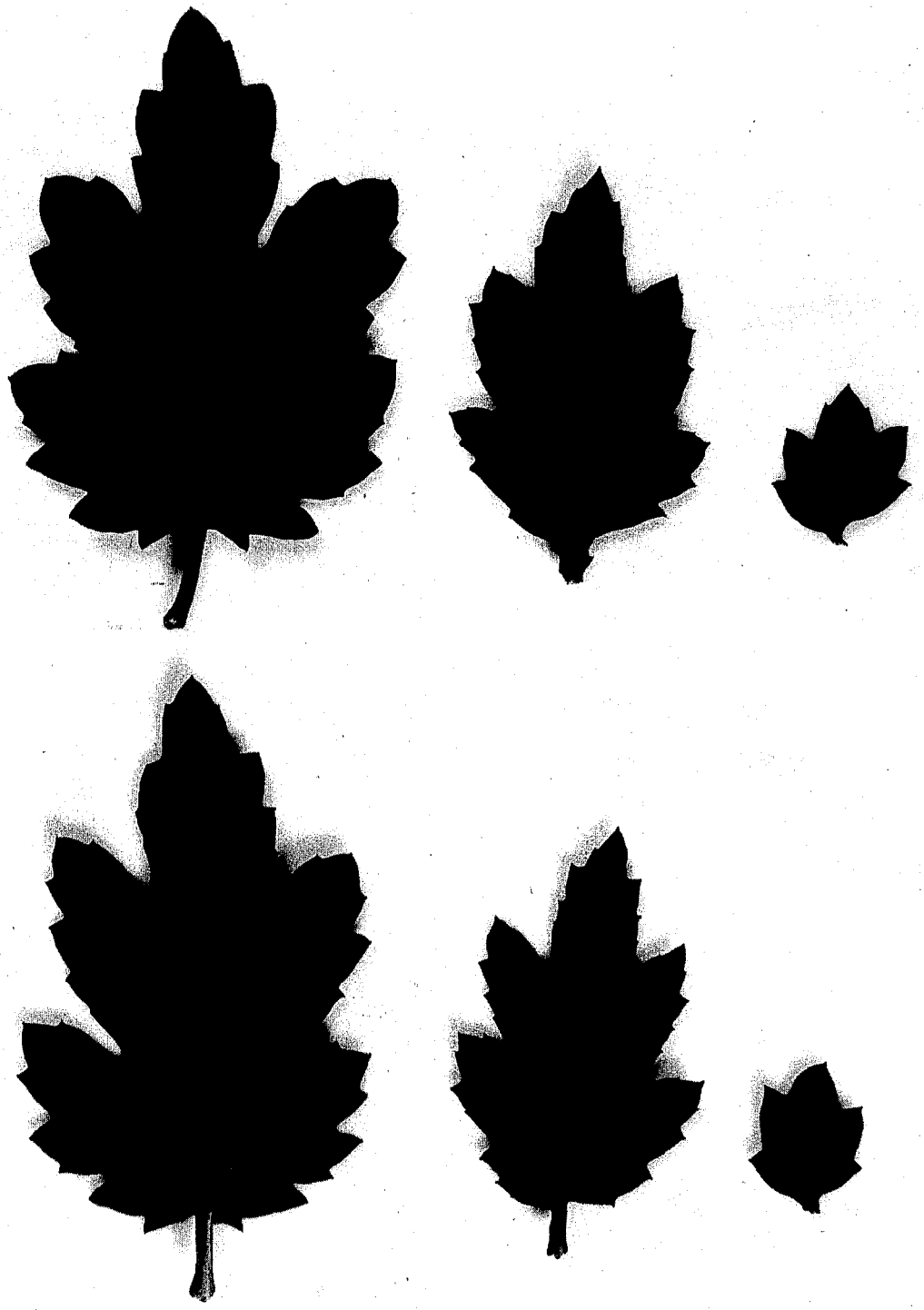

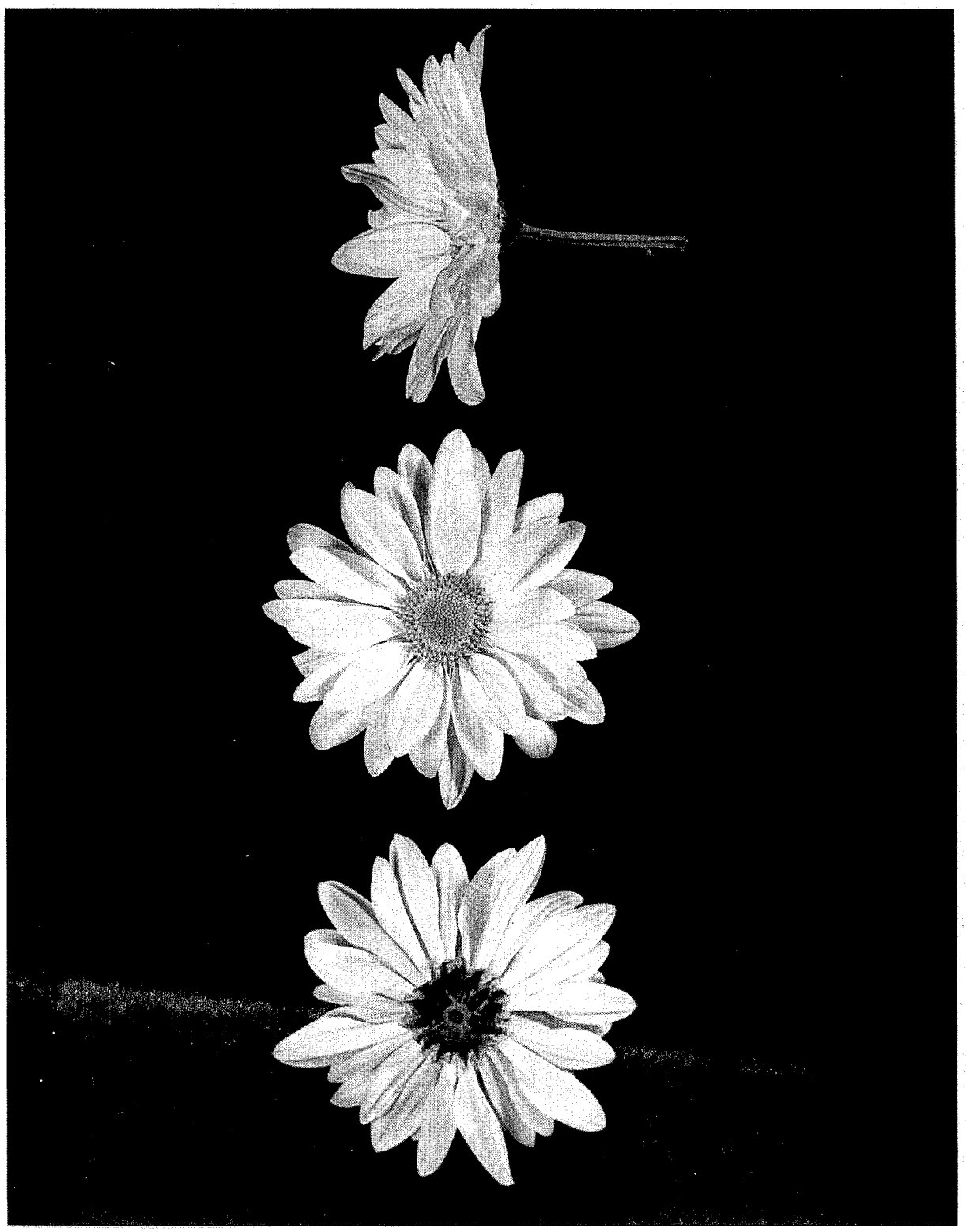

* * * * *